United States Patent
Shapiro et al.

(10) Patent No.: US 9,510,924 B2
(45) Date of Patent: Dec. 6, 2016

(54) APPARATUS AND METHOD FOR INHIBITING STRESS URINARY INCONTINENCE

(71) Applicant: Floelle Inc., Acton, MA (US)

(72) Inventors: Jerrold M. Shapiro, Maynard, MA (US); Cheri A. Grantham, Willis, TX (US)

(73) Assignee: Floelle Inc., Acton, MA (US)

( * ) Notice: Subject to any disclaimer, the term of this patent is extended or adjusted under 35 U.S.C. 154(b) by 269 days.

(21) Appl. No.: 14/043,579

(22) Filed: Oct. 1, 2013

(65) Prior Publication Data

US 2014/0128666 A1    May 8, 2014

Related U.S. Application Data

(63) Continuation of application No. PCT/US2012/031784, filed on Apr. 2, 2012.

(60) Provisional application No. 61/473,955, filed on Apr. 11, 2011.

(51) Int. Cl.
*A61F 2/04*    (2013.01)
*A61F 2/00*    (2006.01)

(52) U.S. Cl.
CPC ........... *A61F 2/0036* (2013.01); *A61F 2/0009* (2013.01); *A61F 2/0013* (2013.01)

(58) Field of Classification Search
CPC ............ A61F 2/00–2/004; A61B 2017/00805; A61B 2018/00523; A61B 17/12022; F16K 31/145; F16K 31/3855
USPC ............................ 600/29–31; 251/4–10, 61.1
See application file for complete search history.

(56) References Cited

U.S. PATENT DOCUMENTS

| | | | |
|---|---|---|---|
| 3,797,478 A * | 3/1974 | Walsh et al. ................ 600/29 |
| 3,810,474 A * | 5/1974 | Cross ................... A61M 16/04 |
| | | | 128/207.15 |
| 4,813,935 A * | 3/1989 | Haber et al. ............. 604/99.02 |
| 5,088,980 A * | 2/1992 | Leighton ..................... 600/30 |
| 5,234,409 A | 8/1993 | Goldberg et al. |

(Continued)

FOREIGN PATENT DOCUMENTS

WO    WO 9602214 A1 *    2/1996

OTHER PUBLICATIONS

International Preliminary Report on Patentability issued on Oct. 24, 2013 for corresponding PCT Application No. PCT/US2012/031784.

*Primary Examiner* — Charles A Marmor, II
*Assistant Examiner* — Thaddeus Cox
(74) *Attorney, Agent, or Firm* — Brian M. Dingman; Dingman IP Law, PC (57) ABSTRACT

An apparatus (60) for use within a woman's urethra (9) for inhibiting urine outflow when her intra-abdominal pressure rises. The apparatus (60) includes a generally tubular device (50) having a proximal end and a distal end and defining a longitudinal axis. Device (50) comprises structure (5) that is constructed and arranged to define a longitudinal passageway (14) that extends entirely through the device (50) from the proximal end to the distal end. Structure (5) is further constructed and arranged to be altered via an increase in intra-abdominal pressure, from a first state in which the passageway (14) is open along its length and able to conduct urine to a second state in which the passageway (14a) is more restricted or is closed off, to inhibit the passage of urine.

15 Claims, 7 Drawing Sheets

(56) References Cited

U.S. PATENT DOCUMENTS

| | | | |
|---|---|---|---|
| 5,782,916 A * | 7/1998 | Pintauro et al. | 623/23.66 |
| 5,906,575 A * | 5/1999 | Conway | A61F 2/0022 600/29 |
| 6,119,697 A * | 9/2000 | Engel et al. | 128/885 |
| 6,464,999 B1 * | 10/2002 | Huo | A61F 2/0022 424/400 |
| 2006/0100478 A1 * | 5/2006 | Connors et al. | 600/29 |
| 2008/0045781 A1 * | 2/2008 | Salama | 600/29 |

* cited by examiner

APPARATUS AND METHOD FOR INHIBITING STRESS URINARY INCONTINENCE

FIELD

This disclosure relates to devices for abating incontinence in women, and in particular to devices that serve to inhibit or prevent the unwanted discharge of urine from the urinary tract.

BACKGROUND

Urinary incontinence, or involuntary urine outflow, affects sixteen percent of women in the United States of America. In about seventy five percent of these women, urinary incontinence occurs when the pressure in their abdomen, called the intra-abdominal pressure, or IAP, rises above a threshold pressure, called IAP1; this is called stress incontinence. In about twenty percent of incontinent women, the detrussor muscle of the urinary bladder involuntarily contracts, producing a sudden urge to urinate; this is called urge incontinence. Women with both stress and urge urinary incontinence are said to have mixed urinary incontinence.

While pharmaceutical treatment is available to relax the detrussor muscle and relieve urge urinary incontinence, there are no pharmaceuticals cleared by the U.S. Food and Drug Administration for treating stress urinary incontinence. Many surgical procedures have been developed to mechanically support the human female urethra or to make it more rigid, but these are expensive, have side effects and are chosen by very few incontinent women. Devices to temporarily block urine flow using a urethral catheter whose proximal end expands inside the bladder need to be replaced every time the woman urinates, and are relatively expensive. Palliative measures, such as wearing an absorbent pad and changing it after every urination, are not only expensive but may leave the skin on the inner thighs wet, leading to abrasions and ulcers; while many pads contain deodorants, the residual urine odor is embarrassing for many incontinent women, leading to restricted social contacts and decreasing their quality of life.

Prior art includes devices inserted through the female urethra into the bladder to seal the bladder neck until the devices are removed, and a device containing a manually operated drainage control valve that is inserted through the female urethra into the bladder as disclosed in U.S. Pat. No. 5,234,409.

SUMMARY

Disclosed herein is an apparatus that automatically inhibits or prevents urinary discharge during sudden elevation of intra-abdominal pressure, which functions without intervention by the user and which does not impede her normal activities.

Among the features of the disclosure may be noted the provision of a female incontinence device which is automatically activated by increased intra-abdominal pressure, a female incontinence device which is entirely contained within the body of the user, a female incontinence device which can be easily installed and removed, a female incontinence device which can be operationally fixed within the female urethra, a female incontinence device which effectively prevents urinary discharge when such discharge is not desired and permits such discharge when the user desires and the intra-abdominal pressure is less than a certain threshold pressure (IAP2), a female incontinence device manufactured of materials which prevent the growth of bacteria on their surfaces, and a method for controlling female stress urinary incontinence and female mixed urinary incontinence.

Other features of the disclosure will be in part apparent and in part pointed out hereinafter. In accordance with the disclosure, the female incontinence apparatus defines a passageway or conduit having inlet and outlet openings for receiving, conducting and discharging urine. The device also includes one or more structures that obstruct this conduit, but only when the pressure on the urethra surrounding it exceeds a threshold pressure (IAP1). These structures define a clear path through the apparatus when the pressure on the urethra surrounding it falls below a threshold pressure (IAP2), and the pressure of urine within the conduit exceeds another threshold pressure (IVP1). In one embodiment, the apparatus is located within the urethra and the structures for obstructing the passageway comprise fluid-filled flexible chambers or balloons which are located such that they are partially in contact with the lining of the urethra. Intra-abdominal pressure elevations caused by, for example, coughing or sneezing, are transmitted through the urethra to such chambers, causing the fluid within them to be displaced. The fluid moving within the chambers causes a part of the chambers to obstruct the flow of urine through the passageway. The fluid within each chamber returns to its initial location once intra-abdominal pressure returns to normal and the pressure of urine inside the passageway as a result of micturition exceeds another threshold pressure (IVP2). The apparatus serves as a flow control valve that is normally open, but is automatically closed by increased intra-abdominal pressure, which typically results from the patient coughing, laughing, lifting, sneezing, etcetera. The apparatus thus inhibits or fully prevents involuntary urine leakage. The apparatus may also include structure that holds the passageway in a selected position within the urethra, ideally such that the proximal part of the device (closest to the urinary bladder) which is in contact with the lining of the urethra is also proximal to the part of the urethra that passes through the musculature of the pelvic floor.

Featured herein is an apparatus for use within a woman's urethra for inhibiting urine outflow when her intra-abdominal pressure rises. The apparatus includes a generally tubular device having a proximal end and a distal end and defining a longitudinal axis. The device comprises structure that is constructed and arranged to define a longitudinal passageway that extends entirely through the device from the proximal end to the distal end. The structure is further constructed and arranged to be altered via an increase in intra-abdominal pressure, from a first state in which the passageway is open along its length and able to conduct urine to a second state in which the passageway is more restricted or is closed off along all or part of its length, to inhibit the passage of urine.

The structure may comprise at least one liquid-filled flexible chamber or balloon. The flexible chambers may extend generally along the longitudinal axis of the device. The chambers may be constructed and arranged to essentially fill the urethra at least at a first location along the longitudinal axis. At the first location the flexible chambers may each define an essentially circular segment shape such that two or more of them together can essentially fill a hollow cylindrical tubular portion of the device. At a different, second location along the longitudinal axis the device may be constructed and arranged such that the flexible chambers each define an essentially annular segment shape.

The device may comprise a frame that has a first tubular section with a first diameter and a second tubular section with a second, larger, diameter, The tubular sections may be interconnected. The tubular sections may be interconnected by a spider member. The device may further comprise at least two liquid-filled flexible chambers, where the flexible chambers extend generally along the longitudinal axis of the device and are constructed and arranged to essentially fill the urethra at least at the location of the second tubular section. The spider may comprise a plurality of thin elongated spider members, and there may be an equal plurality of flexible chambers. The flexible chambers may be coupled to the outside of the first tubular section and the inside of the second tubular section. The apparatus may further comprise a retaining ring coupled to the outside of the second tubular section. Proximate the location of the second tubular section the flexible chambers may each define an essentially circular segment shape. Also, proximate the location of the first tubular section the flexible chambers may each define an essentially annular segment shape.

Also featured herein is an apparatus for use within a woman's urethra for inhibiting or obstructing urine outflow when the pressure in her abdomen rises, and allow more normal urine outflow otherwise. The apparatus has a plurality of at least partially flexible fluid-filled chambers constructed and arranged such that a rise in intra-abdominal pressure causes the fluid in one or more of the chambers to flow.

Still further featured herein is an apparatus for use within a woman's urethra for inhibiting or obstructing urine outflow when the pressure in her abdomen rises, and allows more normal urine outflow otherwise. The apparatus has a flow control valve that defines a longitudinal opening for the passage of urine, wherein the opening is constricted or closed when an increase in the intra-abdominal pressure causes the pressure on the outside of the valve to rise.

This disclosure also features a method of inhibiting or obstructing urine outflow in a woman. The method contemplates providing a flow control valve that defines a longitudinal opening for the passage of urine and is opened and closed via the flow of a control fluid within the valve, and locating the valve in the urethra such that the outside of the valve is in contact with the inside of the urethra. When the intra-abdominal pressure increases, the increase is transmitted through the urethra to the outside of the valve, and causes flow of the control fluid that results in a constriction of the valve's longitudinal opening.

DESCRIPTION OF EMBODIMENTS

Figures 1A, 2A:
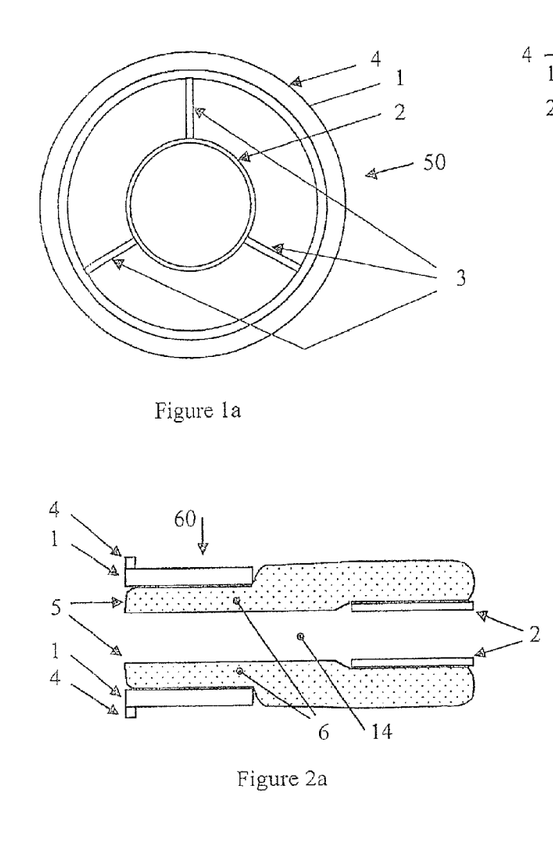
FIGS. 1a and 1b are end and side views, respectively, of the frame of an embodiment of an apparatus that can be used to inhibit stress urinary incontinence in human females.
FIGS. 2a and 2b are longitudinal cross-sectional views of an apparatus that includes the frame shown in FIG. 1, illustrating a position in which urine can pass and a position in which urine flow is occluded, respectively.
Figures 1B, 2B:
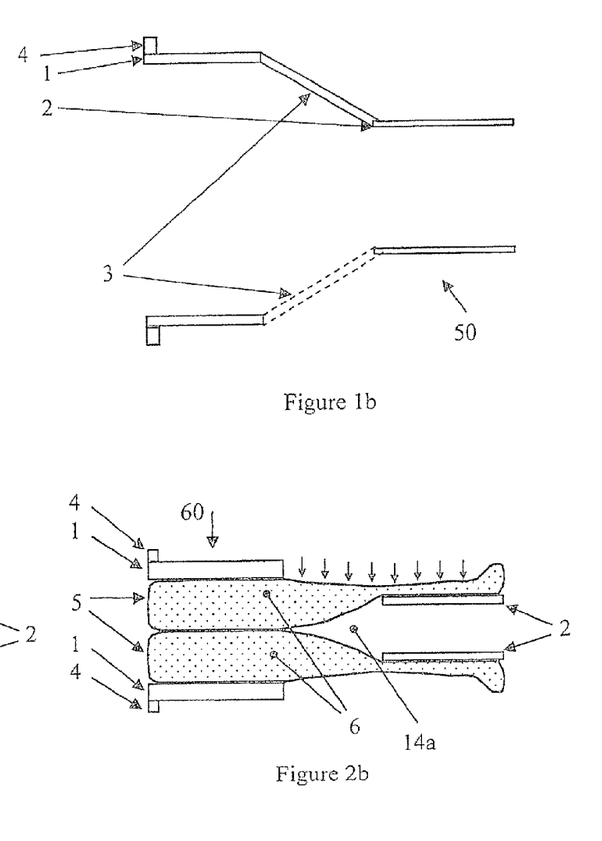

FIG. 1 shows the frame 50 of one embodiment of a device 60 that can be used to inhibit or prevent stress urinary incontinence in a human female. Frame 50 consists of an outer tube 1, an inner tube 2, a spider 3 (with the number of vanes equal to the number of elastic chambers or balloons 5) and a retaining ring 4 all connected to form a semi-rigid structure and possibly manufactured as a single piece. FIG. 1a is a view of frame 50 perpendicular to its long axis and viewed from its distal end when inserted in the urethra of a woman. FIG. 1b is a side view of frame 50. The retaining ring 4 maintains the location of the device along the long axis of the female urethra.

FIG. 2 shows the complete device 60. Frame 50 surrounds two or more flexible balloons or chambers 5 (three in this case) which are filled with a fluid 6 that is preferably a biocompatible fluid with low viscosity, such as isotonic saline solution. Any air or other gas has been removed from the balloons and filling fluid so as to render the fluid incompressible. This embodiment includes three balloons, but the apparatus and method herein contemplates the use of one or more balloons or chambers.

The distal end (nearest the vulva when the device is inside the female urethra) of each balloon in this embodiment is generally wedge shaped (more specifically, generally shaped as a circular segment), such that the distal ends of the balloons as a whole occupy a generally circular cylindrical volume. The outer diameter of this cylinder is approximately equal to the inner diameter of the outer tube 1 of frame 50. The rounded part of the distal portion of each balloon 5 (corresponding to the cylinder's circumference) is attached to the inner surface of the outer tube 1 along part or all of their meeting surfaces. The proximal end (nearest the urinary bladder when the device is inside the female urethra) of each balloon is generally shaped like a sector of an annulus, with the inside diameter of such annulus approximately equal to the outer diameter of the inner tube 2 of frame 50 and attached along all or part of their meeting surfaces. Chambers 5 thus are inhibited from moving longitudinally or rotationally relative to frame 50. The spiders 3 that connect the frame's inner and outer tubes pass between the balloons. The outer diameter of the proximal part of each balloon is almost equal to the inner diameter of the frame's outer tube. The outer diameter of the frame's outer tube is approximately equal to the inside diameter of the human adult female urethra.

The volume of fluid inside each balloon is determined by placing a solid cylindrical rod, whose diameter is slightly less than that of the frame's inner tube and whose length exceeds that of the device, inside the frame's inner tube with one end at the device's proximal end and placing a hollow tube of circular cross-section, whose inner diameter is slightly larger than the outside diameter of the frame's outer tube, with one end at the device's proximal end, then filling the multiple balloons with equal amounts of incompressible fluid until all the balloons are full. Once this fill volume is measured and recorded, it will be used to fill each balloon before the balloon is sealed.

When device 60 is placed in the mid-urethra of a woman, and her intra-abdominal pressure, abbreviated IAP, is low, the balloons will have an arbitrary shape. When the woman initiates the micturition reflex, her bladder's detrusor muscles contract. This causes urine to flow from her bladder through her urethra and through the lumen 14 that is located along the longitudinal axis (not shown in the drawing) of device 60, and exit outside her body. Tube 2 maintains a central entrance opening to the device, into which urine flows from the bladder. The fluid pressure of her urine against the balloons in the location within tube 1 pushes the inner portions of the balloons (corresponding to the points of each balloon's circular segment shaped distal end) away from the device's axis. This creates a full-length lumen or passageway 14 for urine flow. This also displaces the fluid inside each balloon from its distal end toward its proximal end, as shown in FIG. 2a. When the woman is not micturating, but raises her IAP by coughing, laughing, sneezing, jogging, lifting or other means, the raised IAP presses her urethra against the proximal outer surfaces of the balloons above tube 2 (indicated by the arrows in FIG. 2b). This displaces the fluid within the balloons from their proximal ends toward their distal ends. The movement of fluid causes the distal ends of the balloons to each assume a circular segment shape as shown in FIG. 2b, thereby occluding the device lumen 14a where it passes through outer frame 1, thus blocking urine flow through the device. Once the IAP returns to normal, the fluid redistributes within each balloon and allows urine flow during micturition.

To prevent the growth of microbes on the surfaces of the device, an antimicrobial substance can be mixed into the materials before they are formed into the balloons and frame. To prevent urine crystals, if any, from adhering to the device all surfaces of the device in contact with urine can be coated with a highly lubricious material.

Figure 3:
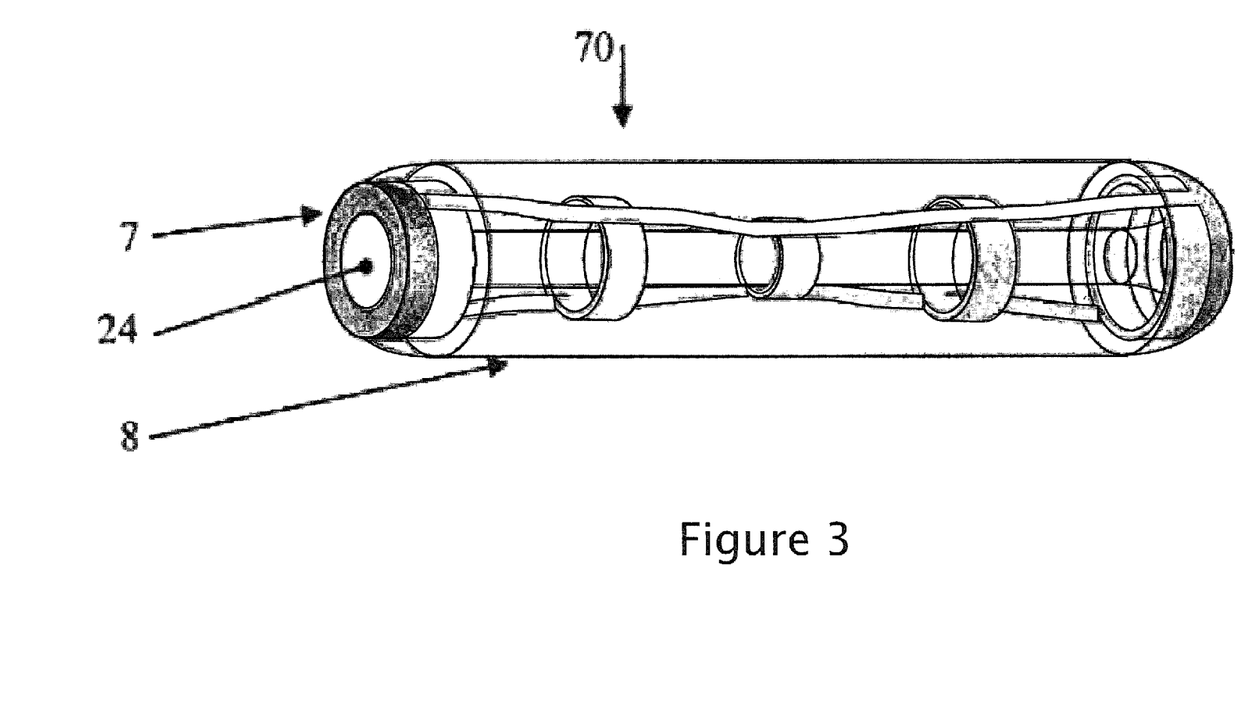
FIG. 3 is a perspective view of a second embodiment of an apparatus that can be used to inhibit stress urinary incontinence in human females.

In a second embodiment, as shown in FIG. 3, the device 70 is fabricated from elastic waterproof material in the shape of a hollow toroid 8 formed from rotating a long rectangle about an axis parallel to and displaced from a long side; a rigid generally hourglass-shaped frame 7 inside the toroid maintains its length and outer diameter at its extremities, while allowing the outer surface of the elastic toroid to be deformed by the adjacent urethra during periods of increased intra-abdominal pressure. The toroid is filled with an incompressible liquid, which may be distilled water, isotonic saline or a fluid whose density and viscosity is equal to or less than that of distilled water at body temperature, 37 degrees Centigrade. When the outer surface of the toroid is pressed inward by the adjacent urethra, the incompressible fluid inside it is displaced and causes the inner surface of the toroid, which normally forms the conduit 24 for urine, to expand into such conduit to narrow the conduit's diameter, greatly increase the conduit's flow resistance (which varies inversely with the fourth power of the conduit diameter) and inhibit or effectively prevent any urine flow through the conduit.

A prototype of this second embodiment consisted of a flexible balloon with an internal channel for urine flow stretched over a rigid plastic frame, as shown in FIG. 3. The device was placed inside a thin-walled elastic tube which simulated the urethra, and whose inner diameter was equal to the outside diameter of the device. Proof of concept testing was performed using a Starling Resistor, which consisted of a pump, the thin-walled elastic tube in an air-tight chamber, and a flow control circuit equipped with a flow meter. The external pressure of the elastic tube, which is the internal pressure of the airtight chamber, was controlled by a rubber bulb and measured by an attached gauge. The flow through the elastic tube was measured by the flow meter. As the average urine flow rate during micturition for females between 14 and 65 years old is between 0.9 and 1.08 L/min, a flow rate of about 1 L/min was used to test the device. The flow registered by the flow meter was recorded as the external pressure on the elastic tube was slowly increased until no flow was registered by the flow meter. This procedure was repeated multiple times.

Figure 4:
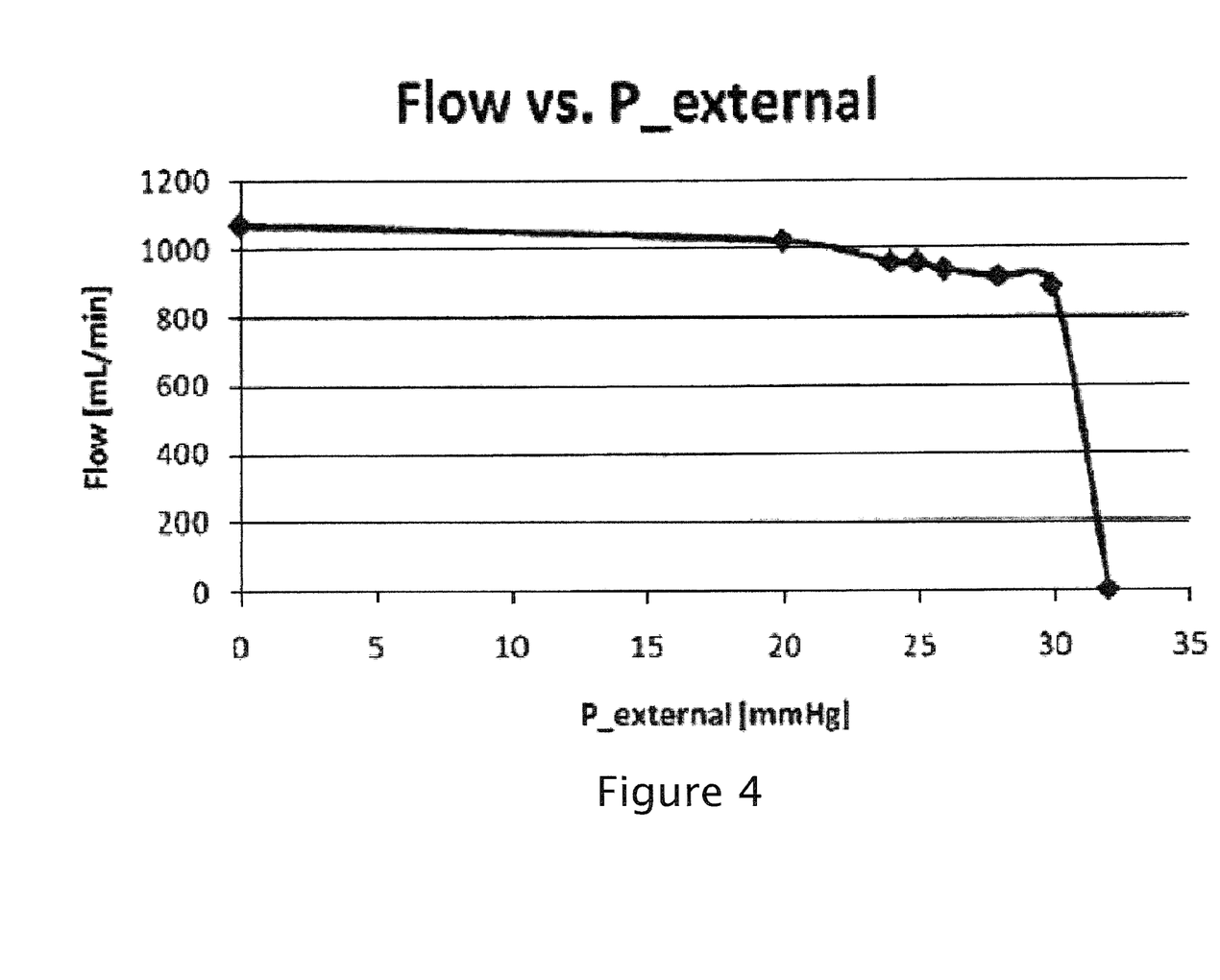
FIG. 4 illustrates the performance of a prototype of the apparatus.

A graph of the average flow rate versus external pressure is shown in FIG. 4. As the external pressure on the elastic tube simulating the female urethra was increased, the flow through the embodiment's conduit decreased until it reached zero flow at 32 mmHg, which is 43.5 cm $H_2O$. This is the external pressure that causes occlusion. While this pressure is greater than the specified occlusion pressure of the device, 30 cm $H_2O$, this value is likely to change when the final device materials are tested. Despite this discrepancy, the results of this test demonstrate that occlusion occurs for physiologic external pressures.

The second embodiment (device 70) can be constructed by connecting together, using adhesives or ultrasonic welding, the ends of a tube of flexible material to form a balloon. We have selected biocompatible materials such as PDMS, a silicone rubber (polydimethylsiloxane), or alternatives like thermoplastic polyurethanes made by Bayer, such as Texin and Desmopan, for the flexible balloon. The more rigid parts of the device can be machined or molded from a biocompatible plastic such as polyetheretherketone (e.g., Zeniva PEEK from Solvay Advanced Polymers LLC in Alpharetta, Ga.) with polysulfone, polyphenylsulfone or polyetherimide as alternative biocompatible plastics, Ionic silver in a zeolite carrier from Agion Technologies in Wakefield, Mass., or equivalent antimicrobial compounds, can be incorporated into these flexible and more rigid materials to give them antimicrobial properties.

Once the rigid frame is inserted inside the balloon, the balloon is filled with one of the sterile liquids described above so that air is excluded, and the balloon is sealed. The device looks like that shown in FIG. 3 and has an overall length of about 25 millimeters, and at low intra-abdominal (IAP) and intravesical (IVP) pressures, an outside diameter of about 3 millimeters and a conduit, passageway or lumen 24 whose inside diameter is about 1.5 millimeters. The thickness of the balloon and its mechanical properties can be selected so that when the intra-abdominal pressure is below about 20 cm $H_2O$, defined as IAP2 above, and the pressure of urine or similar fluid inside the device's conduit is greater than about 40 cm $H_2O$, defined as IVP1 above, then urine will flow through the device's conduit 24 and allow the patient's bladder to empty. When the intra-abdominal pressure is above about 30 cm $H_2O$, defined as IAP1 above, and bladder's detrusor muscles are relaxed, then fluid within the device's flexible balloon will transmit the intra-abdominal pressure to the walls of the device's conduit 24, and cause the conduit diameter to become very small, cause its flow resistance to become very high and effectively obstruct flow through such conduit. This will prevent urine leakage during intra-abdominal pressure spikes due to the patient laughing, coughing, sneezing, lifting, etc.

Figure 5A:
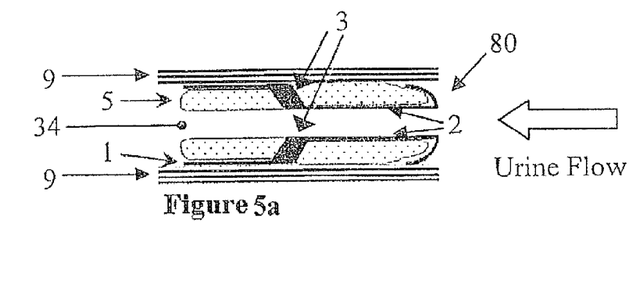
FIGS. 5a-5c are longitudinal cross-sectional views and an end view, respectively, of a third embodiment of the apparatus.
Figure 5B:
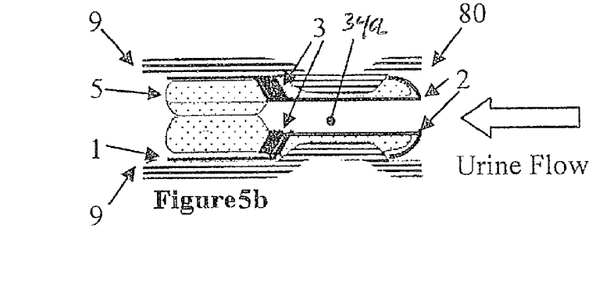
Figure 5C:
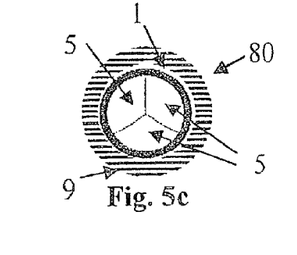

A third embodiment, device 80, is shown in FIGS. 5a, 5b and 5c. As viewed from the urethral meatus (FIG. 5c), the device includes three flexible and elastic chambers 5 constructed of biocompatible elastomer which may contain an antimicrobial substance, such as silver ions; the device cross section resembles a pie cut into three equal slices as shown in the center of FIG. 5c. The chambers run parallel to the long axis of the urethra for about 25 mm; part of the way from the distal to the proximal end of the device, the chamber cross-section changes to surround a hollow conduit 2 whose diameter is about half that of the about 3 millimeter outside diameter of the device established by portion 1. This proximally located tube connects, via a spider 3 of three vanes passing between the three chambers, to a larger hollow tube 1 that surrounds the outside curved surfaces of the three chambers. Each chamber is filled with sterile isotonic saline solution and sealed; each chamber is filled to a predetermined volume so that, at normal intra-abdominal pressure, a lumen 34 can form between the distal apices of the three chambers to allow the outflow of urine.

In FIGS. 5a and 5b, which are not to scale, the striped lines represent the urethra 9; the black lines represent the harder plastic shell comprised of interconnected portions 1, 2 and 3, and the elastic chambers 5 are shown as thin black lines with dots inside to represent the fluid fill. While the urethra of women with stress and mixed incontinence may not be subject to the full amplitude of increases in IAP, the elevated IAP will still exert pressure on the urethral wall, which will be transmitted to the three chambers of the device in the urethral lumen, causing them to move the fluid contained within them from the proximal to the distal end of the device, and to expand that part of the chambers so that they come together to block the device lumen 34a, as shown in FIG. 5b. Due to its low viscosity and volume, we expect the fluid inside each balloon to respond quickly to elevated IAP (typically in the range of 85 to 95 cm $H_2O$) and occlude the urethra during coughs and sneezes. The device will also respond to contraction of the muscular walls of the urethra, part of which contracts under neural control at the start of a sneeze before elevation of the IAP. The elastic chambers' liquid fill volume will be set during the manufacturing process so that the part inside of tube 1 is closed at low IAP and low intra-urethral pressure, but opens at elevated intra-urethral pressure during micturition (typically in the range of 10 to 30 cm $H_2O$). The flexible balloons can be fabricated using the well-known dip molding technique used to make surgical gloves and condoms. The molds can be made of a water soluble material, so that after the silicone material cures, water can be injected into the part to dissolve and wash out the molding material; the balloon interior can be flushed with a solution that kills bacteria, viruses and fungi, flushed again with sterile water then filled with sterile isotonic saline and sealed. The more rigid parts of the device can be machined or molded from a biocompatible plastic, as described above. Ionic silver in a zeolite carrier can be incorporated into these materials to give them antimicrobial properties, also as described above.

Figure 6A:
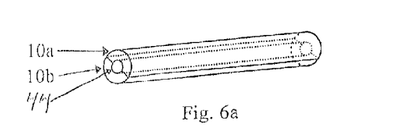
FIGS. 6-9 illustrate the shapes and arrangements of the chambers for an apparatus that uses two, three, four or five liquid-filled chambers, respectively, with figure "a" showing the relaxed position in which a lumen is formed to allow the passage of urine, and figure "b" showing the closed position in which the lumen is restricted or fully closed along at least a portion of its length, to inhibit urine flow.
Figure 6B:
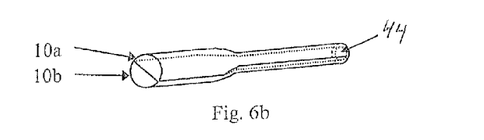
Figure 7A:
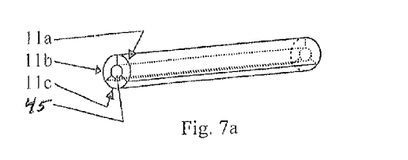
Figure 7B:
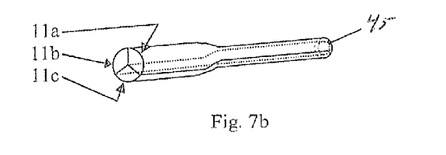
Figure 8A:
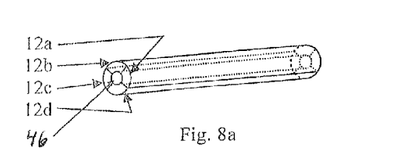
Figure 8B:
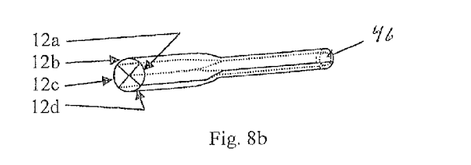
Figure 9A:
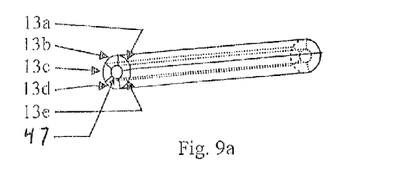
Figure 9B:
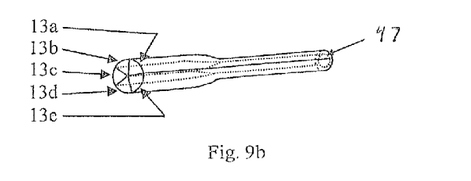

Additional embodiments similar to the second embodiment may be constructed with two, three, four or five (or, conceivably, more if desired) flexible balloons, as shown in FIGS. 6-9, respectively, in which FIGS. 6a-9a show the balloons in their state during micturition, and FIGS. 6b-9b show the same balloons in their state during which the lumen is occluded. These figures show only the balloons and not the frame, which typically includes the spider vanes, an inner tube and an outer tube. The number of vanes typically equals the number of balloons. FIG. 6a shows two balloons 10a and 10b that are each generally semi-circular in cross section and can define lumen 44. FIG. 7a shows three balloons 11a-c that each generally define a ⅓ circular segment in cross section and can define lumen 45. FIG. 8a shows four balloons 12a-d that each generally define a ¼ circular segment in cross section and can define lumen 46. FIG. 9a shows five balloons 13a-e that each generally define a ⅕ circular segment in cross section and can define lumen 47.

All embodiments are inserted into the female urethra inside a short catheter, and held in place while the catheter is withdrawn. As shown in FIG. 1, a retaining ring can hold the device in place. Alternatively, the device could be attached to the distal urethral mucous membrane via a bioadhesive so that it is held in place and thus is neither expelled nor moves into the bladder. If the device needs to be removed, a wire or other member with a short L-shaped hook at the far end may be inserted through the device's inner tube or lumen until it extends beyond the device's proximal end; rotated, pressed against one side of the inner tube then withdrawn until the hook is against the proximal end of the inner tube; a catheter similar to that used to insert the device is inserted into the urethra and advanced until it separates the device from the urethra, then the catheter, device and wire are simultaneously withdrawn.

The embodiments describe the use of circular sector-shaped chamber segments that co-act to close the device lumen when the intra-abdominal pressure rises. However, the apparatus could use other means to channel fluid flow caused by a constriction of the urethra due to an IAP rise. For example, there could be one or more chambers or balloons used, and the chambers could have more arbitrary shapes, so long as the chamber or the multiple chambers fill or essentially fill one location of the inside of the device tube when fluid inside the chamber(s) is moved by the increased IAP.

Figure 10A:
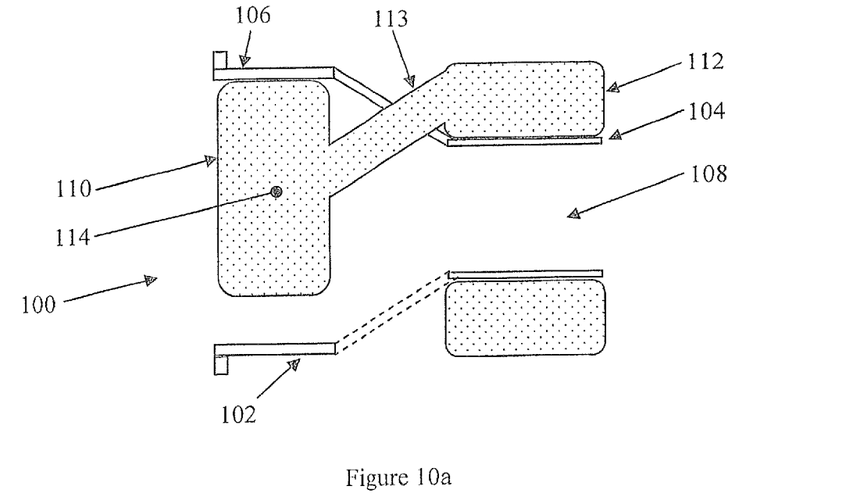
FIGS. 10a, 10b and 10c are views similar to those of FIGS. 5a-5c, for another embodiment that uses only a single chamber.
Figure 10B:
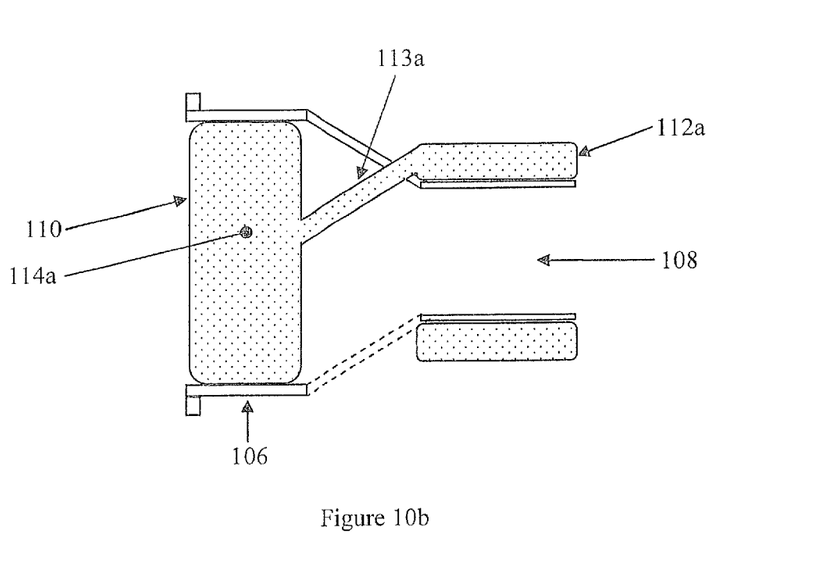
Figure 10C:
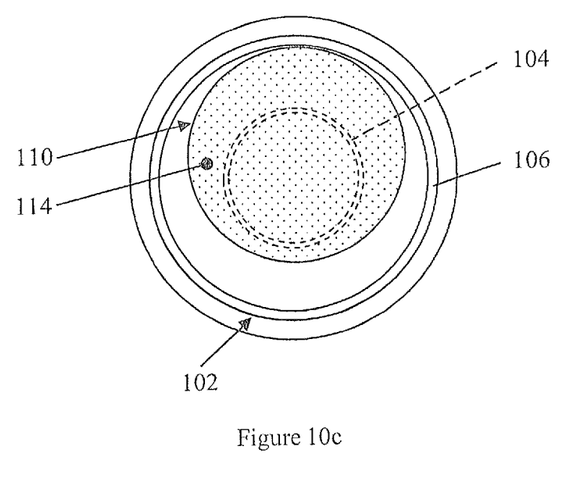

As just one example, there could be a single spherical or cylindrical balloon inside the lumen of the larger frame so that when it is full it touches the inside of the frame (i.e., fills the frame) to block flow, but when it is not full, urine can flow around the outside of the balloon between the balloon and the frame around some or all of the balloon's circumference. A small section of the balloon's circumference could be attached to the inner surface of the frame to prevent the balloon from getting twisted. This design would retain the rigid frame described above, and have the proximal part of the balloon surround most of the inner tube, but with a single connection between the proximal and distal parts of the balloon. An example is shown in FIGS. 10a, 10b and 10c. Apparatus 100 includes frame 102 of the type described above, with outer tube 106 longitudinally displaced from inner tube 104. A single chamber or balloon 110 comprises portion 112 fixed to the outside of tube 104 and portion 114 located within tube 106 and fixed to tube 106 in one location, as shown in the end view of FIG. 10c. Integral connecting portion 113 allows fluid flow between portions 112 and 114. In the "open" position shown in FIGS. 10a and 10c, lumen 108 is open along the entire length of the apparatus. When portion 112 is squeezed by the urethra it collapses into form 112a; this pushes fluid through connecting portion 113a and into portion 114, to create enlarged portion 114a which fills the lumen within tube 106. This blocks urine flow through apparatus 100. The volume of fluid to be placed in the single balloon could be determined by placing a crescent shaped object between the balloon 110 and the outer tube 106 in addition to putting the part 106 inside a cylinder whose inside diameter is slightly larger than that of part 106 and whose length is a least as long as the device along its longitudinal axis, and then inflating the balloon to slightly above local atmospheric pressure.

What is claimed is:

1. An apparatus for use entirely within a woman's urethra for inhibiting urine outflow when her intra-abdominal pressure rises, comprising:
   a generally tubular device having a proximal end and a distal end and defining a longitudinal axis;
   wherein the device comprises structure comprising at least one liquid-filled flexible chamber, where the structure is constructed and arranged to define a longitudinal passageway having a length that extends entirely through the device from the proximal end to the distal end, and a frame that overlies part but not all of each chamber; and
   wherein the structure is further constructed and arranged such that an increase in intra-abdominal pressure causes flow of the liquid in at least one of the at least one chamber, to alter the structure, from a first state in which the passageway is open along its length and able to conduct urine to a second state in which the passageway is more restricted or is closed off, to inhibit the passage of urine.

2. The apparatus of claim 1 wherein the structure comprises at least two liquid-filled flexible chambers.

3. The apparatus of claim 2 wherein the flexible chambers lie along the longitudinal axis of the device and are constructed and arranged to essentially fill the urethra at least at a first location along the longitudinal axis, and wherein the frame overlies the chambers at this first location.

4. The apparatus of claim 3 wherein at the first location the flexible chambers each define an essentially circular segment shape.

5. The apparatus of claim 4 wherein at a second location, different from the first location, along the longitudinal axis the device is constructed and arranged such that the flexible chambers each define an essentially annular segment shape.

6. The apparatus of claim 1 wherein the frame comprises a first tubular section with a first diameter and a second tubular section with a second, larger diameter, where the second tubular section has a location and overlies part but not all of each chamber.

7. The apparatus of claim 6 wherein the tubular sections are interconnected.

8. The apparatus of claim 7 wherein the tubular sections are interconnected by a spider member that has a number of vanes.

9. The apparatus of claim 8 wherein the device comprises at least two liquid-filled flexible chambers, where the flexible chambers lie along the longitudinal axis of the device and are constructed and arranged to essentially fill the urethra at least at the location of the second tubular section.

10. The apparatus of claim 9 wherein the spider member vanes comprise thin elongated vanes, and there are the same number of vanes and flexible chambers.

11. The apparatus of claim 10 wherein the first tubular section has an outside and the second tubular section has an inside, and wherein the flexible chambers are coupled to the outside of the first tubular section and the inside of the second tubular section.

12. The apparatus of claim 11 further comprising a retaining ring coupled to the outside of the second tubular section.

13. The apparatus of claim 12 wherein proximate the location of the second tubular section the flexible chambers each define an essentially circular segment shape.

14. The apparatus of claim 13 wherein proximate the location of the first tubular section the flexible chambers each define an essentially annular segment shape.

15. A method of inhibiting or obstructing urine outflow in a woman with a urethra that has an inside, where the woman has an intra-abdominal pressure, the method comprising:
   providing a flow control valve that defines a longitudinal opening for the passage of urine and is opened and closed via the flow of a control liquid within the valve; and
   locating the valve entirely in the urethra such that the valve is in contact with the inside of the urethra;
   wherein when the intra-abdominal pressure increases, the increase causes flow of the control liquid that results in a constriction of the valve's longitudinal opening.

* * * * *